United States Patent
Feldman et al.

(10) Patent No.: US 9,816,945 B2
(45) Date of Patent: Nov. 14, 2017

(54) SYSTEM AND METHOD FOR DETERMINING PROPERTIES OF LIQUIDS

(71) Applicant: Yissum Research Development Company of the Hebrew University of Jerusalem Ltd, Jerusalem (IL)

(72) Inventors: Yuri Feldman, Jerusalem (IL); Paul Ben-Ishai, Modiin (IL); Alexander Puzenko, Jerusalem (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 14/424,041

(22) PCT Filed: Aug. 28, 2013

(86) PCT No.: PCT/IL2013/050733
§ 371 (c)(1),
(2) Date: Feb. 26, 2015

(87) PCT Pub. No.: WO2014/033719
PCT Pub. Date: Mar. 6, 2014

(65) Prior Publication Data
US 2015/0226683 A1 Aug. 13, 2015

Related U.S. Application Data

(60) Provisional application No. 61/694,357, filed on Aug. 29, 2012.

(51) Int. Cl.
G01R 27/04 (2006.01)
G01N 22/04 (2006.01)
(Continued)

(52) U.S. Cl.
CPC ............ *G01N 22/04* (2013.01); *A01J 5/0133* (2013.01); *G01N 27/023* (2013.01); *G01N 27/06* (2013.01); *G01N 33/06* (2013.01)

(58) Field of Classification Search
CPC .... G01N 27/023–27/025; G01N 27/06; G01N 22/04; G01N 33/06
(Continued)

(56) References Cited

U.S. PATENT DOCUMENTS 4,359,638 A * 11/1982 Allport .................. G01N 33/04
250/358.1
4,414,472 A * 11/1983 Watt ........................ G01N 23/12
250/359.1
(Continued)

FOREIGN PATENT DOCUMENTS

DE          10209889 A1    10/2003
ES          2160468 A1     11/2001
(Continued)

OTHER PUBLICATIONS

T. Hanai et al "Theory of dielectric relaxations due to the interfacial polarization for two-component suspensions of spheres" Colloid & Polymer Science 264:888-895 (Apr. 1986).
(Continued)

*Primary Examiner* — Patrick Assouad
*Assistant Examiner* — Demetrius Pretlow
(74) *Attorney, Agent, or Firm* — Browdy and Neimark, P.L.L.C.

(57) ABSTRACT

At least one property of a complex liquid is determined utilizing first and second sensing devices for measuring a respective first and second physical parameter of the liquid and generating respective first and second measured data indicative thereof. A control unit connectable to the sensing devices is used for analyzing the first and second measured (Continued)

data and determining the at least one property of the complex liquid. The first measured data may be responsive to a relatively low-frequency electric or electromagnetic field induced in the liquid, and the second measured data may be a response of the liquid to a relatively high-frequency external electromagnetic field applied to it.

23 Claims, 8 Drawing Sheets

(51) Int. Cl.
*A01J 5/013* (2006.01)
*G01N 27/02* (2006.01)
*G01N 33/06* (2006.01)
*G01N 27/06* (2006.01)

(58) Field of Classification Search
USPC .................................................. 324/639–640
See application file for complete search history.

(56) References Cited

U.S. PATENT DOCUMENTS

| | | | | |
|---|---|---|---|---|
| 4,902,961 | A | 2/1990 | De et al. | |
| 5,583,432 | A * | 12/1996 | Barnes | G01N 33/49 324/204 |
| 5,625,293 | A * | 4/1997 | Marrelli | G01N 22/04 324/638 |
| 5,798,268 | A * | 8/1998 | Swider | G01N 27/06 422/62 |
| 6,782,736 | B1 * | 8/2004 | Hammer | G01F 23/26 73/304 C |
| 2007/0008060 | A1 * | 1/2007 | Weller | G01N 27/023 336/229 |
| 2009/0267617 | A1 * | 10/2009 | Seyfi | G01N 27/023 324/655 |
| 2010/0235107 | A1 * | 9/2010 | Fukumura | G01N 27/226 702/24 |
| 2011/0267074 | A1 * | 11/2011 | Xie | G01N 33/2823 324/629 |
| 2012/0293186 | A1 * | 11/2012 | Duval | G01N 33/2823 324/649 |
| 2013/0110411 | A1 * | 5/2013 | Black | G01N 27/02 702/23 |

FOREIGN PATENT DOCUMENTS

| | | |
|---|---|---|
| WO | 03048728 A2 | 6/2003 |
| WO | 2011064770 A2 | 6/2011 |

OTHER PUBLICATIONS

T. Hanai "Theory of the Dielectric Dispersion due to the Interfacial Polarization and its Application to Emulsions"The Influence of Ultrasonic Waves on the PH 171: 23-31 (Feb. 1960).
R.M. Matanguihan et al "Dielectric measurement to monitor the growth and the physiological states of biological cells" Bioprocess Engineering 11:213-222 (Nov. 1994).
Ken Mishima et al "On-Line Monitoring of Cell Concentrations by Dielectric Measurements" Journal of Fermentation and Biogengineering 77:4:291-295 (Jul. 1991).
Uwe Pliquett "Bioimpedance: A review for food processing" Food Eng. Rev. 2:74-94 (Mar. 2010).
Arvin S. Quist et al "Elecrical conductances of Aqueous Sodium Chloride Solutions from 0-800 degrees and at Pressures to 4000 Bars $^\wedge$ 1,2". Journal of Physical Chemistry. 72:2: 684-703 (Feb. 1968).
Feldman Y., et al. "Time domain dielectric spectroscopy study of biological systems", IEEE transactions on dielectrics and EI, 10: 728-753 (Jan. 2003).
Zheng, S., et al. "An investigation on dielectric properties of major constituents of grape must using electrochemical impedance spectroscopy", European Food Research and Technology, 229:6: 887-897 Jul. 2009).
Shiinoki Y., et al. "On-line monitoring of moisture and salt contents by the microwave transmission method in a continuous salted butter-making process", Journal of Food Engineering, 38:2: 153-167(Aug. 1998).
Asami K., et al. "Dielectric spectroscopy of biological cells", Bioelectrochemal Bioenergy, 40:141-145 (Jan. 1996).
Asami, K., et al. "Real-time monitoring of yeast cell division by dielectric spectroscopy", Biophysical Journal, 76:1: 3345-3348. XP002935266 (Jun. 1999).
Wakamatsu H. "A Dielectric Spectrometer for Liquid Using the Electromagnetic Induction Method", Hewlett-Packard Journal, 48:2 : 37-44 (Apr. 1997).
Anderko A. et al "Computation of Electrical Conductivity of Multicomponent Aqueous Systems in Wide Concentration and Temperature Ranges", Industrial & Engineering Chemistry Research, 36:5: 1932-1943 (May 1997).
Janzekovic M., et. al. "Mastitis detection based on electric conductivity of milk", Journal of Achievements in Minerals and Manufacturing Engineering, 34:1: 39-46 (May 2009).
Zywica, R., et al."An attempt of applying the electrical properties for the evaluation of milk fat content of raw milk", Journal of Food Engineering, 111:2: 420-424. XP028476676 (Jan. 2012).
Mukhopadhyay, S. C., et al "A Low-Cost Sensing System for Quality Monitoring of Dairy Products", IEEE Transactions on Instrumentation and Measurment, 55:4: 1331-1338. XP055002523 (Aug. 2006).

* cited by examiner

SYSTEM AND METHOD FOR DETERMINING PROPERTIES OF LIQUIDS

FIELD OF THE INVENTION

This invention is generally in the field of sensing techniques, and relates to sensing system and method for determining properties of liquids. More particularly, the present invention provides for monitoring of specific physical and/or chemical properties and conditions of multi component liquids, such as colloidal and electrically conductive liquids.

REFERENCES

The following references may be useful for understanding the background of the invention:
1. *"Time domain dielectric spectroscopy study of biological systems."*, Yuri Feldman et al., IEEE transactions on dielectrics and EI, 2003, v. 10, 728-753;
2. *"A Review for Food Processing"*, Pliquett Uwe, Food Engineering Reviews Volume: 2 Issue: 2 Pages: 74-94 (June 2010);
3. "An investigation on dielectric properties of major constituents of grape must using electrochemical impedance spectroscopy", Zheng Sicong et al., European Food Research And Technology Volume: 229 Issue: 6 Pages: 887-897 (October 2009);
4. "On-line monitoring of moisture and salt contents by the microwave transmission method in a continuous salted butter-making process", Shiinoki Y et al., Journal Of Food Engineering Volume: 38 Issue: 2 Pages: 153-167 (November 1998);
5. *"Dielectric measurement to monitor the growth and the physiological states of biological cells"*, Matanguihan R M et al., Bioprocess Engineering Volume: 11 Issue: 6 Pages: 213-222 (November 1994);
6. *"Online monitoring of cell concentrations by dielectric measurements"*, Mishima K et al., Journal Of Fermentation And Bioengineering Volume: 72 Issue: 4 Pages: 291-295 (1991)

BACKGROUND OF THE INVENTION

Inspection and monitoring of various properties and conditions of a substance is essential in various technical fields, including production processes of said substance. For example, dielectric spectroscopy may be used for inspecting and monitoring biological cells, such as monitoring and imaging cell growth in fermentation as described by Asami et al., in *"Dielectric spectroscopy of biological cells"*, 1996, Bioelectrochem. Bioenerg. 40:141-145

A system for real time measurement and control of humidity in dielectric fluid substances is described in Patent Publication No. ES 2160468, wherein absorbed microwave energy passed through a dielectric material is used to estimate water content of the material in real time during an industrial process.

GENERAL DESCRIPTION

There is an important advantage in allowing onsite real-time determination of physical and/or chemical properties and conditions of a liquid substance during intermediate stages of the substance' production, as liquid materials used in the production process are streamed and processed on a production line. For example, such onsite real-time monitoring may allow quick determination of various characterizing features (qualities) of the liquid substance, as typically needed, for example, in cosmetics, dye, oil and petrol, industries, and in the monitoring of biological materials during food production processes (e.g., milk in the milking or dairy product line). Such real-time characterization of the liquid substance may advantageously allow fast and efficient determination of further processing stages needed in the production process, accordingly.

The inventors of the present invention developed a novel technique for onsite monitoring and characterizing in real time liquid substances during production thereof and/or while the liquids are being processed. In a broad aspect of the present invention the liquid is examined utilizing measurement data comprising a first response of the liquid to an electric field induced in the examined liquid, said first response of the liquid being indicative of a first physical parameter of the liquid, and a second response of the liquid to an externally applied electromagnetic field, said second response being indicative of a second physical parameter of the liquid. In some embodiments the first response of the liquid is responsive to a relatively low-frequency electric field induced in the liquid, and the second response is a response of the liquid to a relatively high-frequency externally applied electromagnetic field.

In some possible embodiments a stream of liquid, or a portion thereof, is examined by measuring at least one electrical parameter and at least one microwave scattering parameter of the examined liquid. Characterizing features of the examined liquid may be then determined based on the measured parameters. For example and without being limiting, the response of the examined liquid to an electrical field induced in the liquid may be used to determine electrical conductivity, admittance and/or, permittivity of the liquid. In another non limiting example response of the examined liquid to an externally applied electromagnetic radiation is used to determine electromagnetic absorbance and/or reflectivity of the liquid.

Accordingly, the present invention provides for quick and effective determination of one or more properties of a complex liquid indicative of the liquid' quality. The terms multi component fluid and complex liquid as used herein generally refer to a mixture of at least one liquid substance with one or more other substances, including, for example, colloidal liquids, conductive liquids, and any liquid mixture including a liquid substance and at least another solid or fluid substance. The term property as used herein refers to physical or chemical property or condition of the complex liquid.

The invention utilizes in some embodiments thereof concurrent and independent measurement of at least two different physical parameters of a complex liquid, and processing and analyzing of the measured data and accordingly determining physical and/or chemical properties and conditions of the liquid. The invention may be therefore utilized for real time inspection of the complex liquid during its progress on a production line. The physical and/or chemical properties and conditions determined using the technique of the present invention include those that cannot be directly measured by one-type sensor or at least cannot be measured in real time during the liquid flow through a region of interaction with a sensor.

The present invention in some embodiments thereof relates to system and method for determining properties of a complex liquid in real time, using an arrangement of sensing devices. For example, in possible embodiments of the present invention the sensing devices are utilized for inspection and characterization of milk quality, as it is extracted from the cow teat during the milking process.

One aspect of the present invention relates to a system for determining at least one physical property (e.g., electrical impedance or conductivity, permittivity) or chemical condition (e.g., salt content, fat content, etc.) of a complex liquid (also referred to herein as 'examined liquid'). The system comprises: a sensing device configured and operable for carrying a first measurement of a first physical parameter (e.g., electrical impedance/conductivity) of the complex liquid and generating first measured data indicative thereof, and a second measurement of a second physical parameter (e.g., absorbance or reflectivity of electromagnetic radiation) of the complex liquid and generating second measured data indicative thereof, and a control unit connectable to the sensing device for receiving and analyzing the first and second measured data and determining the at least one physical property or chemical condition of the complex liquid.

In exemplary embodiments of the present invention, the sensing device includes separate first and second sensing units for measuring the first and second parameters, and either includes a third sensing unit for temperature measurements or receives this data from an external device. The first sensing unit may be configured and operable for measuring a first response of the liquid to an induced electric field, said first response being indicative of a first physical parameter of the liquid; and the second sensing unit may be configured and operable for measuring a second response of the liquid to an externally applied electromagnetic field, said second response being indicative of a second physical parameter of the liquid. For example and without being limiting, the first sensor unit may be configured and operable for measuring the first response (e.g., a relatively low-frequency response) of the liquid to an electric (or electromagnetic) field induced in the liquid, and the second sensor unit may be configured and operable for measuring the second response (e.g., a relatively high-frequency response) of the liquid to an externally applied electromagnetic field.

The first sensor unit may be configured and operable for measuring the first physical parameter of the liquid while interacting with a flow of the liquid (e.g., while being in contact with/immersed in the examined liquid). For example and without being limiting, the first sensor unit may comprise at least one pair of induction coils configured and operable to induce an electric (or electromagnetic) field to the liquid flow (i.e., to a region in the vicinity of the sensor where the liquid flows) and measure responsive induction voltage signals indicative of the induced field. Alternatively, the first sensor unit may comprise a plurality of the inductively coupled coils configured and operable to concurrently induce in the liquid flow a plurality of such different electric fields covering a predefined band of relatively low frequencies and measure a respective plurality of induction voltage signals indicative of the induced electric fields. The control unit may be configured to determine the at least one parameter based on the plurality of measured induction voltage signals.

The second sensor unit may be configured and operable for contactless measuring the second physical parameter of the liquid (i.e., with no interaction with the liquid flow). For example and without being limiting, the second sensor unit may comprise at least one electromagnetic transceiver (transmitter and receiver) arrangement configured and operable to measure the electromagnetic radiation absorbance and/or reflectivity of the liquid. Thus, the second sensor unit is configured to apply an electromagnetic field of a relatively high frequencies/frequency range to the liquid.

In some embodiments, a frequency range of the relatively low-frequency field(s) is selected to minimize a dielectric losses component of a complex dielectric permittivity of the liquid and thus ensure that the electrical (voltage) response of the liquid mainly characterizes the electric conductivity of the liquid.

The relatively high-frequency electromagnetic field applied by the second sensor unit may be selected for determining at least one of S11 (reflection coefficient) and S21 (transmission coefficient) parameters of the liquid by detection of phase shifts and magnitudes of microwave signals transmitted through the liquid.

In some embodiments, the sensing units (at least the first and second sensing units) are embedded into a common housing of the sensing device. In some implementations the sensing device has a cavity adapted to receive a sample of the examined liquid, and/or allow streaming of the examined liquid therethrough, for carrying out the measurements. The control unit may be configured to communicate with the sensing device over wires, or optionally via wireless communication means, and is adapted to receive and process the measured data and determine the at least one physical property or chemical condition. The control unit may be further adapted to output (e.g., to a display device) one or more of the measured data indications, the at least one determined physical property and/or chemical condition, and/or output control signals (e.g., to a production unit) generated based thereon.

The control unit may be configured and operable to determine the permittivity of the liquid based on the liquid response to the second, relatively high-frequency, electromagnetic field, and the measured temperature of the liquid. Additionally or alternatively, the control unit may be configured and operable to determine at least one of the droplet size and the interfacial polarization of the liquid based on the liquid response to the induced, relatively low-frequency, electric field and the measured permittivity of the liquid (measured by the second sensor). The control unit may be also configured and operable to determine at least one of the water and fat content of the liquid based on the determined permittivity. In some applications, the control unit is configured and operable to determine at least one of the electrical conductivity and the salt content of the liquid based on the liquid response to the induced relatively low-frequency electric (or electromagnetic) field and preferably also the measured temperature of the liquid.

For example and without being limiting, the control unit may be configured and operable to determine the electrical conductivity of the liquid based on one or more measurements of electrical signals (e.g. voltages and/or currents) induced at the measurement coil of the first sensor by the liquid response to the induced relatively low-frequency electric (or electromagnetic) field. In some applications, the electrical conductivity is determined based on two or more of the electrical voltages (e.g., using a differential computation and/or curve fitting techniques) corresponding to the liquid responses to the first field applied at respective two or more sufficiently close relatively low-frequencies.

For example, and without being limiting, the control unit may be configured and operable to select a frequency range of the relatively low-frequency field that effectively minimizes a dielectric losses component of the complex dielectric permittivity of the liquid and thus ensure that the electrical (voltage) response of the liquid mainly characterizes the electric conductivity of the liquid. Proper selection of the frequency range of said relatively low-frequency field facilitates determination of the electrical conductivity of the examined liquid using a differential computation technique, as will be described herein later in detail.

In some embodiments, the at least one property may include at least one of the following: electric impedance, electric conductivity, permittivity, interfacial polarization, droplet size, salt content, water content and fat content. The control unit may be configured and operable to determine a suitable processing for the liquid based on the at least one property and generate control signals for processing the liquid by the system accordingly.

In another aspect there is provided a method for monitoring at least one physical property or chemical condition of a complex liquid, the method comprising:

concurrently and independently measuring signals indicative of at least two physical parameters (e.g., electrical impedance/conductivity, reflectivity or absorbance of electromagnetic radiation) of the examined liquid and generating corresponding first and second measured data; processing the measured data and determining the at least one physical property (e.g., fat or oil content) or chemical condition (e.g., salt level/salinity) in the examined liquid; and generating data indicative thereof. The method may comprise rejecting the examined liquid if at least one of the determined physical property or chemical condition is different from an acceptable value (e.g., the salinity is higher than acceptable), and directing the examined liquid to a suitable tank (e.g., for further processing) if the at least one physical property or chemical condition is acceptable. The further processing may include low or high fat (or oil) content processing, and the method may further comprise determining fat/oil content in the examined liquid and directing the examined liquid to low or high fat/oil content processing based on the fat/oil content.

The system of the present invention may be easily embedded as an integral part of the piping system used for flowing a collected or processed complex liquid into a storage tank. Thus, the invention may be used for determining quality relating parameters of the complex liquid as it is being streamed through the piping system, and for example appropriately sorting the fluid based on the inspection results by directing the streamed liquid to respective containers according to the quality parameters determined. These features allow using the present invention for process control purposes by onsite real-time inspection and monitoring of the determined at least one physical property and/or chemical condition of liquid(s) streamed in the production lines without interrupting the production process.

By way of example, the system of the present invention may be used to control a manifold of pipes and valves connecting a milking teat cup (e.g., situated in a milking shed for the milking of cows, goats, and/or any other milking mammals) to the storage tank and used for determining milk quality parameters, such as, but not limited to, fat or salt concentration within a milked batch. Upon detection of such quality parameters the batch of milk may be directed to an appropriate tank for further production processing, or disposed of (in case of unacceptable quality).

According to yet another aspect there is provided a piping system defining a main path for streaming a complex liquid therethrough, the piping system comprising: a sensing device accommodated in the vicinity of said main path and being configured and operable for measuring first and second physical parameters of the liquid and generating first and second measured data indicative thereof, and a control unit connectable to the sensing device for receiving and analyzing the first and second measured data, determining at least one property of the complex liquid, and generating data indicative of quality of the liquid thereby enabling generation of sorting data of the liquid while being streamed through the piping system.

According to yet another aspect there is provided a system for determining at least one property of a complex liquid, the system comprising a sensing device configured and operable for measuring first and second physical parameters of the liquid and generating respective first and second measured data indicative thereof, the sensing device comprising a first sensor unit configured and operable for measuring a first response of the liquid to an induced, relatively low-frequency electric (or electromagnetic) field, said first response being indicative of said first physical parameter, and a second sensor unit configured and operable for measuring a second response of the liquid to a second applied, relatively high-frequency external electromagnetic field, said second response being indicative of said second physical parameter, and a control unit connectable to said sensing device for receiving and analyzing the first and second measured data and determining the at least one property of the complex liquid.

According to some embodiments, the first sensing unit is configured for determining electrical impedance (and/or electrical conductivity) of the examined liquid based on measurements of relatively low frequencies (e.g., in frequencies range of 10 Hz to 100 kHz, or sub-ranges within this range) electrical current (or voltage) induced through the liquid. The first sensing unit may be comprised of at least first and second inductance coils, preferably configured as toroidal coils, or having a mutual toroidal core (e.g., ferrite core) thus enabling the examined liquid to flow through the toroidal structure of the coils. For example and without being limiting, measurements obtained using the first sensing unit (first measured data corresponding to low frequency measurements) and temperature measurements may be used for calculating the electrical impedance/conductivity of the examined liquid. In exemplary embodiments of the present invention, the content of salts in the examined liquid is determined based on the determined electrical impedance and the temperature of the examined liquid.

In some possible embodiments of the present invention, the second sensing unit is configured for measurements of absorption (or reflection) of high frequency electromagnetic radiation (e.g., frequencies of about 2 to 70 GHz, or sub-ranges within this range) of the examined liquid e.g., using a microwave sensor (for instance, but not limited to, MR 113D40M Moisture meter, manufactured by Microradar Ltd of Minsk, Belarus). For example and without being limiting, the absorption (or reflection) measurement obtained using the second sensing unit and the temperature measurement obtained using the third sensing unit can be used for calculating water content based on the dielectric permittivity of the examined liquid determined using the response of the liquid to the externally applied high frequency field. In exemplary embodiments of the present invention the fraction of solids in the examined liquid is evaluated based on the dielectric permittivity of the examined liquid enabling determination of fat content in the liquid.

Thus, the system of the present invention may include the first sensing unit comprising at least primary and secondary coils configured for relatively low frequency measurement of electric current (or voltage) induced by the coils configuration within the examined liquid, the second sensing unit comprising a relatively high frequency transmitter and receiver (e.g., using the MR 113D40M Moisture meter mentioned hereinabove, or suchlike) configured for detecting phase shifts and magnitudes of electromagnetic signals upon transmission thereof through the examined liquid, and possibly also the third sensing unit configured for measuring the temperature of the examined liquid.

In possible embodiments of the present invention, a level of interfacial polarization is also determined based on the fraction of self assembled structures in the examined liquid and on the induced relatively low frequency electric current (or voltage) measurements obtained. Optionally, a droplet size (e.g., fat or oil droplet size) in the examined liquid is determined based on the determined level of interfacial polarization.

In one exemplary embodiment of the present invention there is provided an onsite method for monitoring and inspecting properties of a batch of milk as it is being ejected from a milked cow based on determination of electrical impedance, dielectric permittivity and temperature, of the milk batch. The dielectric permittivity may be determined based on measurements of reflectivity (or absorbance) of relatively high frequency electromagnetic radiation and on measurements of the temperature of the examined milk, and the electrical impedance or low frequency dielectric permittivity may be determined based on measurements of relatively low frequency electrical current (or voltage) induced within the examined milk.

The measured and determined milk properties may be used to manipulate a manifold of pipes and valves for directing the milk to a suitable container. For example and without being limiting, the salt content of the milk batch may be determined based on the electrical impedance, and if the determined salt level is too high (e.g., indicative of Mastitis in the milked cow) the manifold state may be changed to direct the milk batch to a draining duct or container for disposal. If the determined salt level is acceptable and low fat content is evaluated based on the water content as determined from the high frequency reflectivity/transmission measurements, the manifold state may be changed to direct the milk batch to a skimmed milk container. Otherwise (i.e., salt level is acceptable and high fat content is determined), the milk batch is directed for further processing (e.g., cheese production, butter production, or suchlike), for example, according to a fat droplet size property determined based on the high frequency reflectivity and on the low frequency inductance measurements.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A and 1B are block diagrams generally illustrating a monitoring system according to possible embodiments of the present invention for monitoring/measuring the properties and quality of a complex liquid, wherein FIG. 1A is a simplified illustration of the system, and FIG. 1B exemplifies possible components of a control unit of the monitoring system;

FIG. 2A to FIG. 2H schematically illustrate possible embodiments of a sensing unit of the present invention for measurements of induced low frequency electrical current (or voltage) usable for determining electric impedance of a liquid, wherein, FIG. 2A illustrates a sensing unit with two coils wound on two identical coaxial toroidal cores, FIG. 2B illustrates a sensing unit with two coils wound on a single toroidal core, FIG. 2C schematically illustrates a sensing unit with two coils wound on two concentric toroidal cores of different diameters, FIG. 2D depicts geometrical parameters of a possible embodiment of the sensor unit shown in FIG. 2C and possible magnetic activation thereof, FIG. 2E schematically illustrates physical concept of the induction sensor shown in FIG. 2B (also applicable to other configurations) and exemplifies measurement of electrical current/voltage induced in the coils, FIG. 2F exemplifies possible circuitries usable for applying and acquiring signals using the coils of the sensing unit, FIG. 2G exemplifies circuitry usable for receiving electric signals from the secondary coil, and FIG. 2H exemplifies circuitry usable for generating electric input signals for the primary coil;

It is noted that the embodiments exemplified in the figures are not intended to be in scale and are in diagram form to facilitate ease of understanding and description.

DETAILED DESCRIPTION OF EMBODIMENTS

The present invention in some of its embodiments provides system and method for determining at least one physical property or chemical condition of a complex liquid based on measurements of physical parameters and/or conditions obtained using different types of measured data acquired concurrently and independently. In one embodiment of the present invention the measured data includes: reflectivity (or absorbance) of high frequency electromagnetic radiation in the examined liquid; induced low frequency electrical current (or voltage); and temperature of the examined liquid. The sensing device of the present invention is configured to concurrently and independently measure various physical parameters and/or conditions of the examined liquid, and based thereupon, to determine the at least one physical property or chemical condition. The at least one determined physical property or chemical condition may include salt content, solid fraction (e.g., determined based on interfacial polarization), fat content, fat droplet size, inductance, and electrical impedance or conductivity. The at least one physical property or chemical condition may be used to control the state of a manifold of pipes and valves used for directing the examined liquid to a suitable container or pipe for further processing.

Figure 1A:
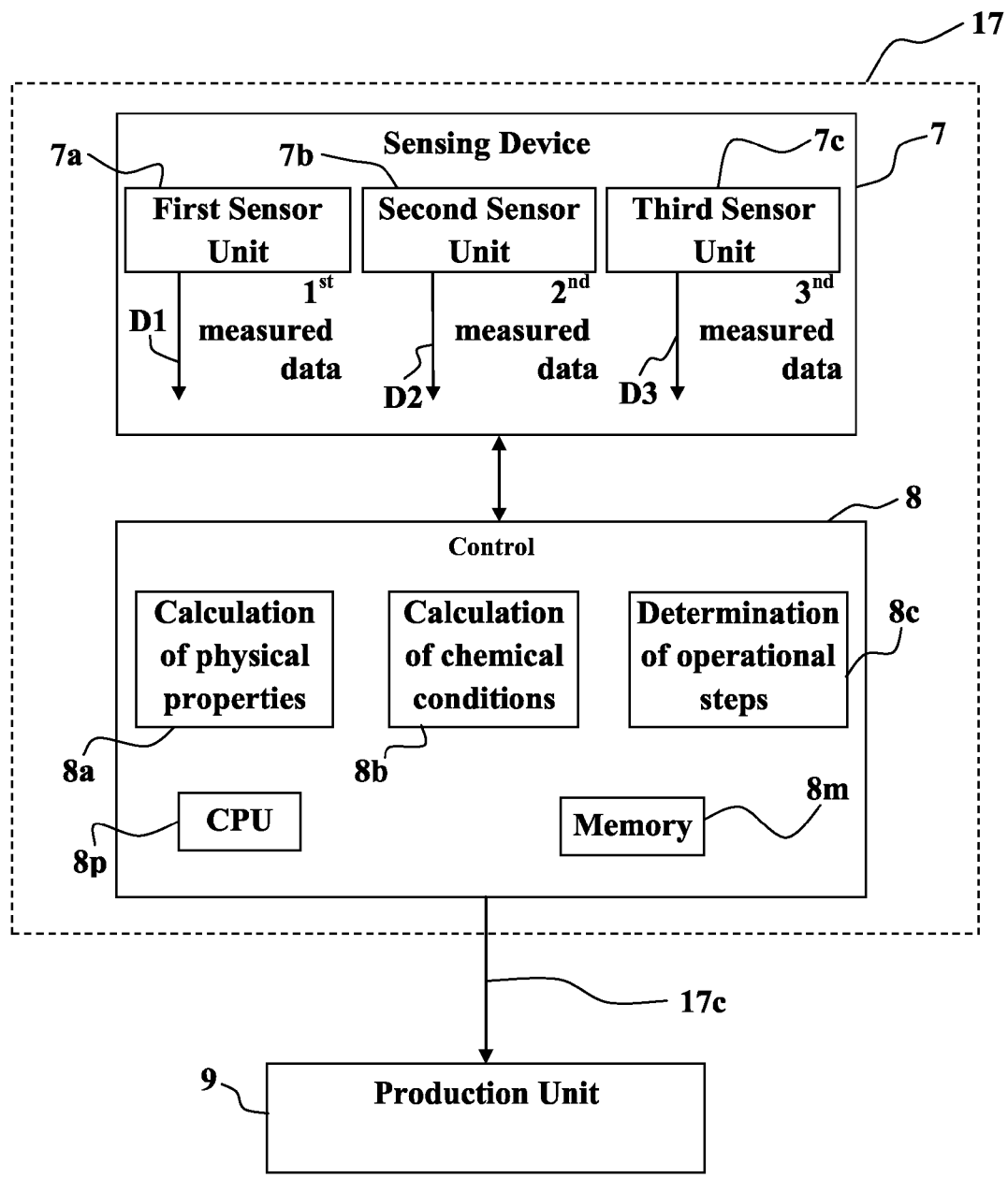

FIG. 1A is a block diagram generally illustrating a monitoring system 17 according to possible embodiments of the present invention. System 17 includes a sensing device 7 and a control unit 8 connectable to the sensing device 7 (by wires or wireless signal transmission, as the case may be).

The sensing device 7 may comprise first and second sensor units, 7a and 7b adapted to measure different signals indicative of physical parameters of the examined liquid and generate corresponding measured data in a format suitable for transmission to the control unit 8 for processing. The sensing device 7 preferably also includes a third sensing unit 7c for measuring one or more additional conditions of the liquid.

The control unit 8 is adapted to receive from sensing device 7 measured data, D1 D2 and D3, indicative of measured physical parameters of an examined liquid. The control unit 8 is typically a computer system including inter alia a processor utility 8p and a memory utility 8m. The processor utility 8p is preprogrammed to receive input data corresponding to the measured data from sensing device 7 and carry out signal processing and calculations usable for determining and evaluating the at least one physical property (8a) or chemical condition (8b) of the examined liquid. Control unit 8 may be further configured to determine various operational steps (8c) based on the measured data, D1 D2 and D3, and/or the determined chemical condition (8b) and/or the physical property (8a).

As will be described below, first, second and third sensor units, 7a 7b and 7c, may be adapted to respectively measure electrical current (or voltage) obtained in the examined liquid responsive to an magnetic/electromagnetic field induced through the examined liquid, reflectivity (or absorbance) of electromagnetic radiation, and temperature.

Figure 1B:
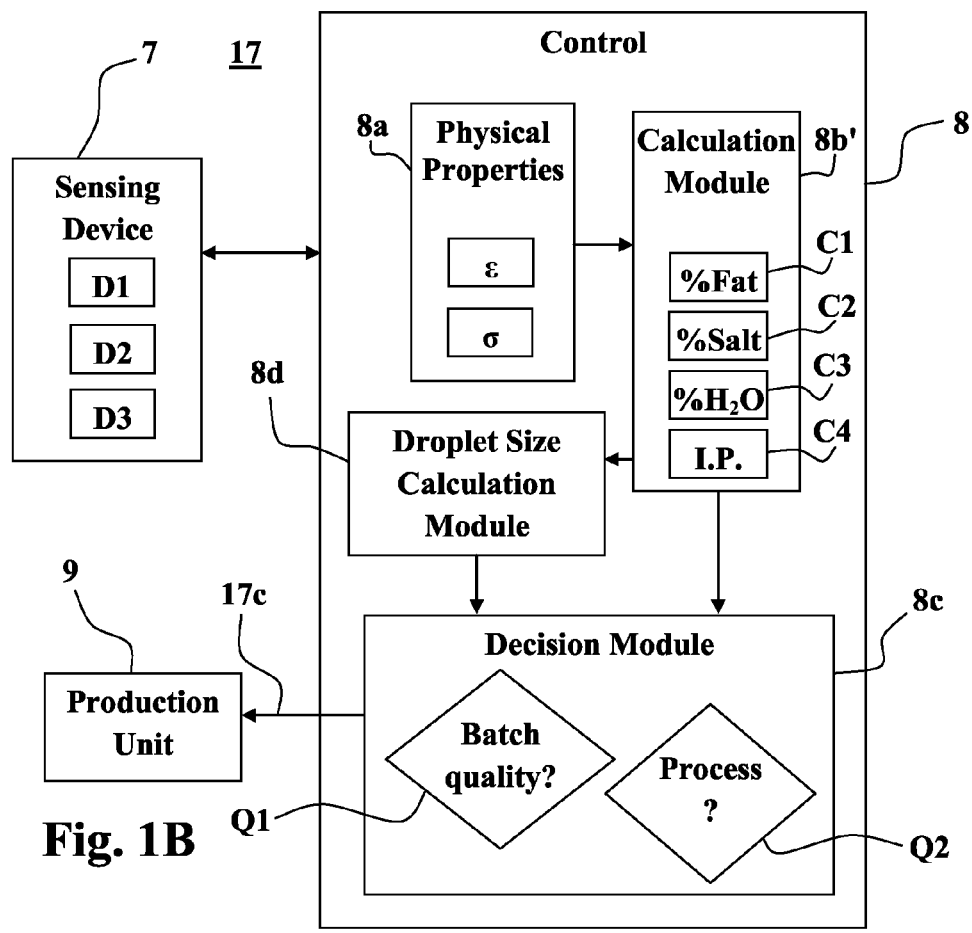

FIG. 1B is a block diagram illustrating the control unit 8 according to some possible embodiments. In this non limiting example, the electrical voltage (or current) D1, the reflectivity (or absorbance) D2, and the temperature D3 related measured data pieces, produced by the sensor units, 7a 7b and 7c respectively, are processed by a physical property calculation module 8a provided in the control unit 8 to calculate at least one of electrical conductivity a and dielectric permittivity c of the examined liquid. A calculation module 8b' provided in the control unit 8 is configured and operable for calculating, based on data calculated in the physical property calculation module 8a and on the measured temperature data D3, at least one of the following chemical conditions: fat (or oil) content C1, salt content C2, and water content C3, of the examined liquid. The calculation module 8b' may be further configured and operable to compute interfacial polarization (I.P.) C4 of the examined liquid (e.g., based on measurements obtained by application of magnetic/electromagnetic field to the liquid).

A decision module 8c may be provided in the control unit 8 to determine quality parameters Q1 and further processing steps Q2, based on data determined in the calculation module 8b'. In possible embodiments of the present invention, determination of the quality parameters Q1 and further processing steps Q2 are determined in the decision module 8c based on data determined in the physical property calculation module 8a and/or the calculation module 8b'. Control unit 8 may further issue control signals 17c to operate the production unit 9 based on the quality parameters Q1 and/or further processing steps Q2 determined in the decision module 8c.

The control unit 8 may further include a droplet size calculation module 8d configured to determine fat (or oil) droplet size based on data determined by the calculation module 8b' and the measured electrical induction signal D1 from the sensing device 7. As exemplified in FIG. 1B, the decision module 8c may use the droplet size determined in the droplet size calculation module 8d for determining the quality parameters Q1 and/or further processing steps Q2, and accordingly, the control signals 17c issued by the control unit 8c may be also based on droplet size determined by the droplet size calculation module 8d.

It is noted that data processing carried out in any of the modules 8b' 8c and 8d may utilize one or more (or all) of the measured data indications (D1 D2 and/or D3) received from sensing device 7.

The following are some examples of the sensor units suitable to be used in the embodiments of the present invention. To facilitate understanding, the same reference numerals are used for identifying components that are common in all the figures.

Figure 2A:
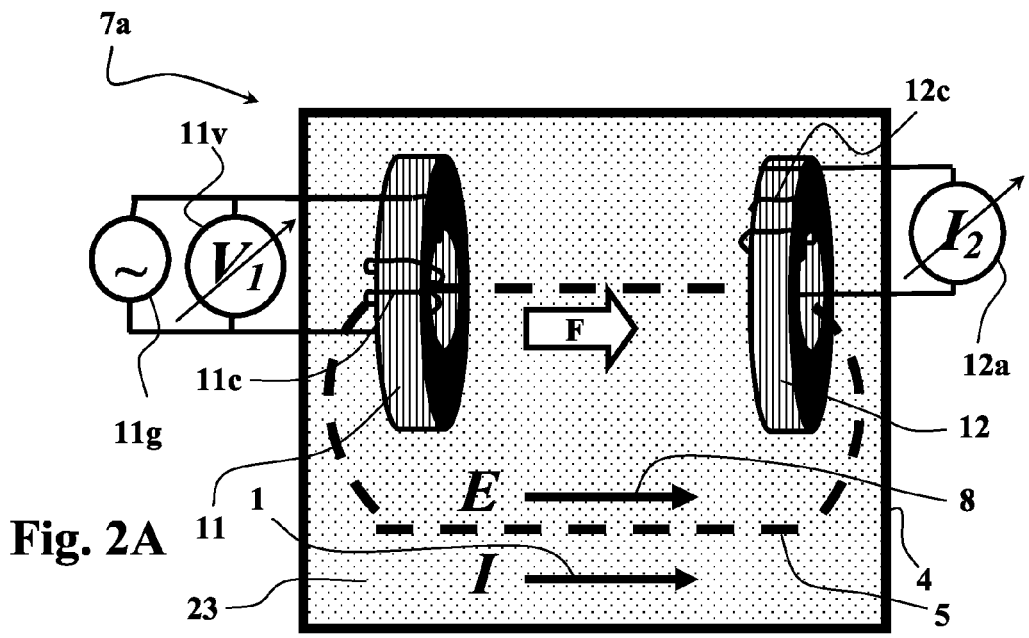

FIG. 2A schematically illustrates an example of the sensor unit 7a which is a measuring unit configured for measuring induced low frequency (e.g., 10 Hz to 100 kHz, or any specified sub-range within this range) electrical voltage (or current). In this exemplary embodiment, measuring unit 7a comprises first and second electromagnetic coils 11c and 12c reeled over respective magnetic cores 11 and 12 and configured to induce an electric field in the examined liquid 23 and to measure an induced electrical voltage (or current) signals based on magnetic induction.

In some embodiments the sensor unit 7a may be configured as a small inductive probe (e.g., an epoxy resin-coated inductive probe) formed by two concentric ferrite toroidal cores with the respective wire coils 11c and 12c inductively coupled through the surrounding medium (examined liquid 23) held in, or streamed through, a measurement zone 4 (e.g., inside a pipe).

When an alternating (AC) voltage $\tilde{V}_1$ (11v) is applied by power source 11g over the primary coil 11c, a magnetic flux is induced in the first core 11, which in turn induces an electric field 8 in the surrounded liquid media 23 along the cyclic field lines 5 passing between the cores 11 and 12. The electric current 1 in the liquid 23 is driven by the electric field 8. The electric current passing through the primary coil 11c induces a magnetic flux in the second core 12, which in turn induces the current $I_2$ (12a) in the coil 12c of the second core 12, that is measured by the ampere meter 12a.

The electrical voltage/current measured at the secondary coil 12c is being indicative of an electric or electromagnetic field induced in the examined liquid 23 by the primary coil 11c in response to an alternating electrical current (e.g., 10 Hz to 100 kHz) supplied to it by the power source 11g. More particularly, magnetic field induced in the torriodal core 11 by the primary coil 11c induces an alternating electric field E in the liquid 23 which is indicative of the dielectric properties of the liquid. The electric field E in the liquid 23 also induces a magnetic field in the core 12 of the secondary coil 12c, which in turn induces an electrical current in the secondary coil 12c that is measured using the current meter $I_2$. The secondary coil 12c thus reacts to the alternating magnetic field induced in the secondary core 12 by the electric field, E, in the liquid 23, that is induced by the primary coil 11c, and to polarization of the examined liquid 23 in response to the electric (or electromagnetic) field induced in the examined liquid 23. Accordingly, the alternating electrical current induced in the secondary coil 12c and measured by the current meter $I_2$ is influenced by the electric (or electromagnetic) field E induced in the liquid 23 and can be therefore used to determine the dielectric properties of the examined liquid 23.

The electrical impedance of the circuit formed by the liquid sample 23 with the two coils 11c and 12c may be determined based on the induced electric current I2 measured by the ampere meter 12a, and the electric voltage V1 applied by the power source 11g over the primary coil 11c. For example, and without being limiting, the admittance Yx of this electric circuit may be computed and used for determining the relative permittivity and impedance of the sample, e.g., as described by K. Asami et al., in "Real-Time Monitoring of Yeast Cell Division by Dielectric Spectroscopy", Biophys. J. 76(1999) 3345-3348.

The cores 11 and 12 may be fabricated from any material suitable for use as a magnetic core, such as, but not limited to, Ferrite. The cores (if used) may be of any suitable shape (i.e., assume any suitable cross-section geometry). The coils may be prepared using a wire made of copper, for example, or from any other suitable electrically conducting wire. The diameter of the wires, the number of turns, and cores geometry, may be determined according to system requirements and conditions e.g., according to geometric dimensions of the system pipes or containers, type of complex liquid used, and suchlike. The electric voltage $V_1$ applied over the primary coil 11c may generally be in the range of few millivolts to several volts. However, electric voltage $V_1$ may be of greater magnitudes if so needed (e.g., 10 to 100 volts), and it may similarly be applied over the other coil 12c such that the induced current (or voltage) may be measured using the coil 11c.

Figure 2B:
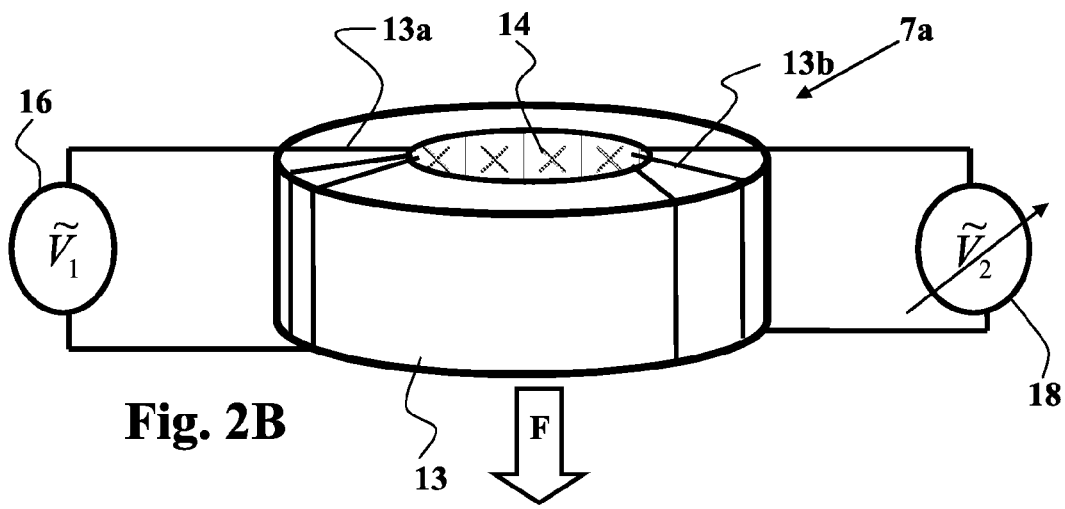

FIG. 2B schematically illustrates another possible embodiment of the present invention of a low frequency sensor unit (measuring unit) 7a for measuring electrical current (or voltage) induced within the examined liquid responsive to an applied magnetic field using a transformer design configuration. This embodiment utilizes a toroidal core 13, possibly having a rectangular cross-sectional shape, over which primary coil 13a and secondary coil 13b are reeled-up.

Core 13 may be fabricated from any material suitable for use as a magnetic core, such as, but not limited to, Ferrite, and may assume any suitable cross-sectional geometry. Coils 13a and 13b may be prepared using a wire made of copper, for example, or from any other suitable electrically conducting wire. The wire diameter, number of turns, and core geometry, may be determined according to system requirements and conditions e.g., according to geometric dimensions of the system pipes or containers, type of complex liquid used, and suchlike. The electric voltage $V_1$ applied over the primary coil 13a by the power source 16 may generally be in the range of millivolts to several volts. However, electric voltage $V_1$ may be of greater magnitudes if so needed (e.g., 10 to 100 volts), and it may similarly be applied over the secondary coil 13b, and the induced current in such case may be measured using the primary coil 13a.

As seen in FIG. 2A and FIG. 2B the toroidal configuration of coils 13a and 13b permits conducting measurements on a liquid while it flows through the circular cavities of the toroidal cores (indicated by arrows F). Measurements of physical conditions and/or chemical properties of a streamed liquid may be carried out effectively with the sensing device 7 of the invention as long as the liquid flowing therethrough is laminar. In case turbulent flow conditions evolve, the reliability of the measured data may be degraded and further processing and/or measurements may be required. For this purpose, sensing device 7 may include additional sensing utilities (not shown) for determining the flow conditions of the examined liquid, or at least for indicating when turbulent flow conditions are evolving.

Figure 2C:
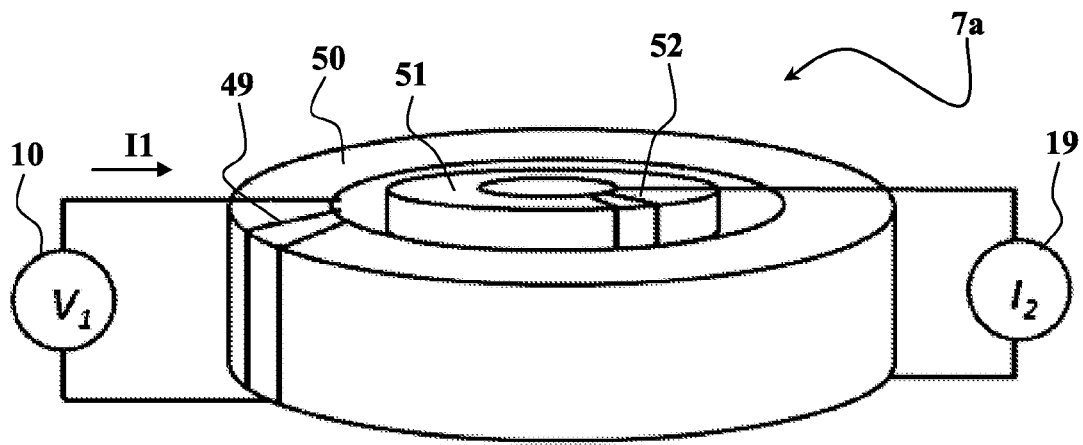

FIG. 2C schematically illustrates another possible example of the sensing unit 7a having a first coil 49 and a second coil 52 wound on two respective first and second concentric toroidal cores 50 and 51 having different diameters. In this example the second core 51 is disposed inside the cavity of the first toroidal core 50 of the sensing unit 7a. As demonstrated in FIG. 2C, AC voltage $V_1$ from the voltage source 10 is applied to the coil 49 of the first toroidal core 50, and the electric current $I_2$ thereby induced in the second coil 52 of the second toroidal core 51 is measured by the ampere meter 19.

By way of example, sensor unit 7a may be implemented using methods and techniques described by H. Wakamatsu in "*A Dielectric Spectrometer for Liquid Using the Electromagnetic Induction Method*", April 1997 Hewlett-Packard Journal, Article 8, the disclosure of which is incorporated herein by reference.

Figure 2D:
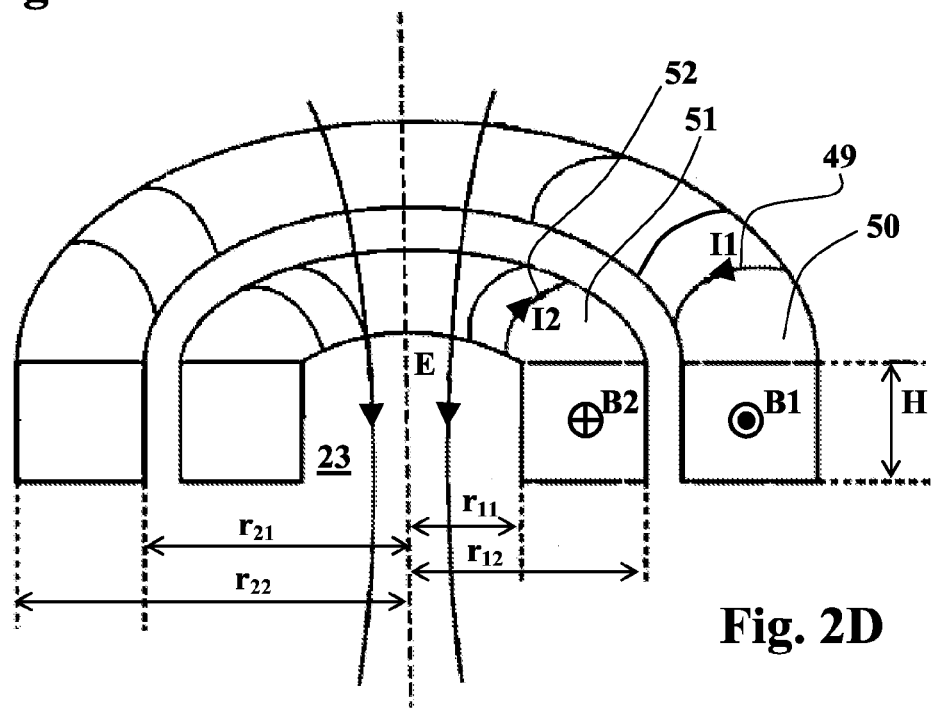

FIG. 2D schematically illustrates the geometrical parameters and physical principles of operation of the sensing unit 7a as exemplified in FIG. 2C. According to the Maxwell's Equations, when an alternating (AC) electric voltage $V_1$ is applied to the first coil 49, an electric current $I_1$ evolves in the first coil wire. The alternating (AC) electric current $I_1$ induces within the first core 50 a cyclic magnetic flux characterized by the vector of the magnetic displacement $B_1$. In turn, the cyclic magnetic flux $B_1$ induces a cyclic magnetic flux $B_2$ in the second core 51 due to which an alternating electric current $I_2$ evolves in the second coil 52. Due to the induced alternating electric current $I_2$ a corresponding alternating electrical field E evolves in the examined liquid 23. This electric field E is interacting with liquid sample 23. Due to the interaction, displacement and conductive electric currents flow occur in the liquid sample 23. According to the Maxwell's Equations, the complex dielectric permittivity $\in^*_c$ is related to the transient admittance $Y=I_2/V_1$ by the following equation—

$$Y = \frac{I_2}{V_1} = -i\omega \frac{W_1 W_2}{R_1 R_2} \cdot d \cdot h \cdot \frac{\beta_1 \frac{\alpha_2}{1-\alpha_2}}{1 - \alpha_1\left(1 - \frac{\alpha_2}{1-\alpha_2}\right)_1} \quad (1)$$

wherein $W_1$ and $W_2$ are the numbers of the turns in the first and second coils, correspondingly; $R_1$ and $R_2$ are resistances of the first and second coils, correspondingly;

$$\beta_1 = 1/a_1, \alpha_1 = \frac{b}{a_1}, \alpha_2 = \frac{b}{a_2},$$

$$a_1 = \frac{2\pi\langle r_1 \rangle}{\mu_0 \mu^*}, a_2 = \frac{2\pi\langle r_2 \rangle}{\mu_0 \mu^*}, b = \frac{1}{2}\omega^2 \varepsilon_0 \varepsilon_c^* \frac{hd}{h+d}\pi \cdot r_{11}^2,$$

$$\langle r_1 \rangle = \frac{r_{11}+r_{12}}{2}, \langle r_2 \rangle = \frac{r_{21}+r_{22}}{2}, d = r_{12}-r_{11} = r_{22}-r_{21}$$

h is the height of the cores with the rectangular cross section, $\in_0$ and $\mu_0$ are the dielectric and magnetic permittivity of the free space, correspondingly; $\in_c^*$ is the relative complex dielectric permittivity of the examined liquid 23 including the DC-conductivity, σ[S/m], term, wherein $\in_c^*$ may be expressed as follows:

$$\varepsilon_c^*(\omega, T) = \varepsilon^*(\omega, T) - i\frac{\sigma(T)}{\varepsilon_0 \omega} = \varepsilon'(\omega, T) - i\left[\varepsilon''(\omega, T) + \frac{\sigma(T)}{\varepsilon_0 \omega}\right], \quad (2)$$

μ* is the relative complex magnetic permeability of the core; ω is circular frequency, and i ($i^2=-1$) is the imaginary unit.

Figure 2E:
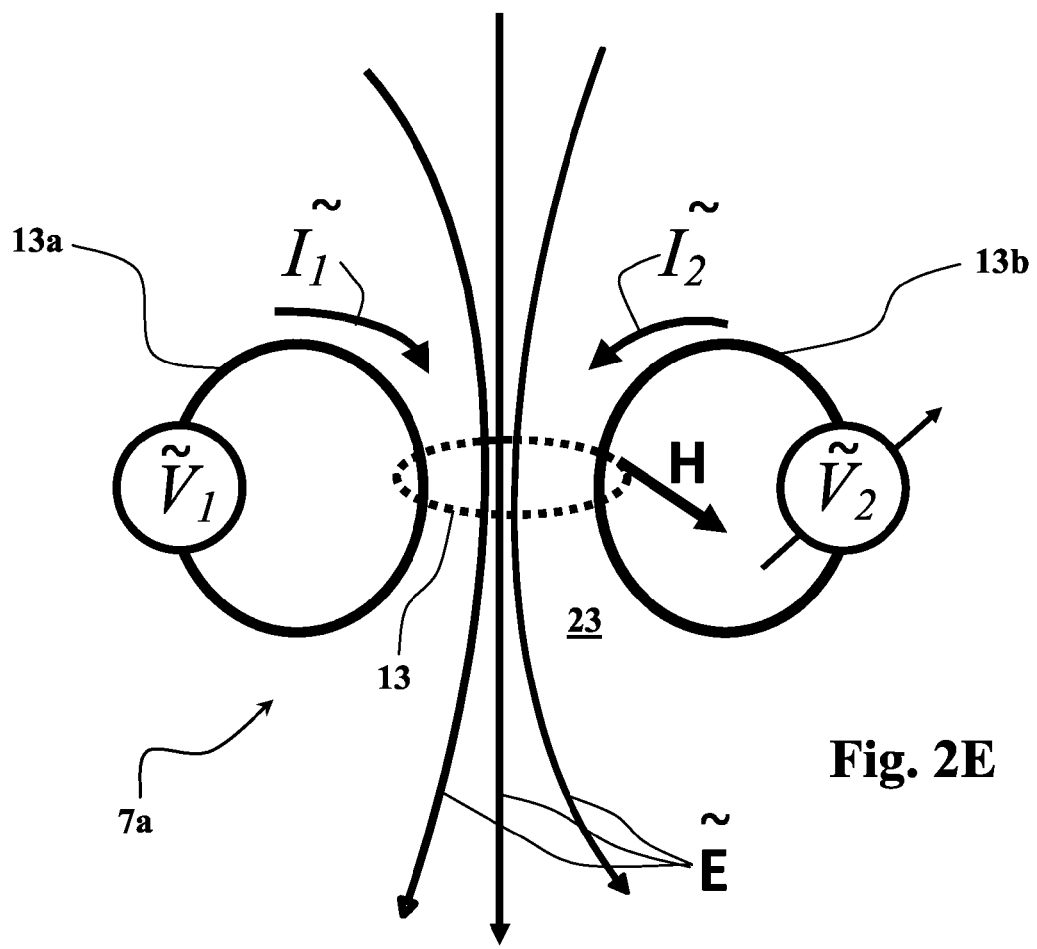

FIG. 2E demonstrates the physical principles of the operation of the sensing unit 7a configured as exemplified in FIG. 2B. According to the Maxwell's Equation, when an alternating (AC) electric voltage $\tilde{V}_1$ is applied over the primary coil 13a, an electric current $\tilde{I}_1$ evolves in the primary coil wire. The alternating (AC) electric current $\tilde{I}_1$ induces within the core 13 a cyclic magnetic flux characterized by the vector of magnetic field force H. In turn, the cyclic magnetic flux H induces an alternating electric current $\tilde{I}_2$ in the secondary coil 13b, and a corresponding alternating electrical field E thus evolves in the examined liquid 23. This electric field E is interacting with liquid sample 23, which may be maintained in a sample holder placed in the cavity of the toroid(s), or which may be streamed through the cavity. As a result of the interaction, displacement and conductive electric currents flow occur in the liquid sample 23.

Thus, a portion of the magnetic flux is conveyed for inducing electric current in the secondary coil 13b, while another portion for inducing the displacement and conductivity electric currents, in the liquid sample. The displacement and conductivity currents depend on the dielectric dispersion of the examined liquid, such that the voltage $\tilde{V}_2$ evolving in the secondary coil 13b is dependent on the dielectric properties of the examined liquid 23.

In case the electric voltage source, designated in FIG. 2E by $\tilde{V}_1$, supplies harmonic signals $\tilde{V}_1(\omega) \sim \exp(-i\omega t)$, the following formula may be used to express the voltage transformation coefficient $\tilde{K}(\omega)$, obtained based on Maxwell's Equations:

$$\tilde{K}(\omega, T) = \frac{\tilde{V}_2(\omega, T)}{\tilde{V}_1(\omega, T)} = \frac{W_2}{W_1} \cdot \frac{1}{1 + \tilde{Q}(\omega, T)}, \text{ where} \quad (3)$$

$$\tilde{Q} = \frac{1}{2} \omega^2 \varepsilon_0 \mu_0 \varepsilon_c^*(\omega, T) \mu^* h d \frac{r_1}{r_2} \quad (4)$$

wherein the notations are as defined hereinabove except for the following:

$W_1$ is the number of turns in the primary coil 13a;
$W_2$ is the number of turns in the secondary coil 13b;
T is the temperature of the examined liquid 23;
$r_1$, $r_2$, and h are the geometrical parameters of the core 13, i.e., the inner and outer radii $r_1$, $r_2$, and height h respectively; $d = r_2 - r_1$.

As follows from Equation (4) above, for the low frequencies, if $\omega \to 0$, then $\tilde{Q}(\omega) \to 0$. In this limit, Equation (3) is reduced to the known voltage transformation coefficient defined only by the ratio of the numbers of turns in the primary and secondary coils:

$$\tilde{K}(\omega \to 0) = \frac{\tilde{V}_2(\omega, T)}{\tilde{V}_1(\omega, T)}\bigg|_{\omega \to 0} \cong \frac{W_2}{W_1}. \quad (5)$$

For the higher frequencies, the factor $$\frac{1}{1 + \tilde{Q}(\omega, T)}$$

represents the correction of the low frequency transformation coefficient in equation (5) due to the displacement current and the DC-conductivity current in the sample (e.g., 5 in FIG. 2A). The relative complex dielectric permittivity $\in_c^*$ of the examined liquid may be therefore determined from equations (3) and (4) as follows:

$$\varepsilon_c^*(\omega) = \quad (6)$$

$$\frac{2\tilde{Q} \cdot r_2}{\omega^2 \mu_0 \mu^* \cdot h \cdot d \cdot r_1} = 2\left(\frac{W_2}{W_1} \cdot \frac{\tilde{V}_1(\omega, T)}{\tilde{V}_2(\omega, T)} - 1\right) \cdot \frac{r_2}{r_1} \cdot \frac{1}{\omega^2 \varepsilon_0 \mu_0 \mu^* \cdot h \cdot d}.$$

where the real part of the relative complex dielectric permittivity $\in_c^*$ is—

$$\varepsilon'(\omega, T) = 2\text{Re}\left[\left(\frac{W_2}{W_1} \cdot \frac{\tilde{V}_1(\omega, T)}{\tilde{V}_2(\omega, T)} - 1\right) \cdot \frac{r_2}{r_1} \cdot \frac{1}{\omega^2 \varepsilon_0 \mu^* \cdot h \cdot d}\right] \quad (7)$$

and the imaginary part (consisting of the dielectric losses, $\in''(\omega,T)$, and the conductivity, $\sigma(T)$) is—

$$\varepsilon''(\omega, T) + \frac{\sigma(T)}{\varepsilon_0 \omega} = -2\text{Im}\left[\left(\frac{W_2}{W_1} \cdot \frac{\tilde{V}_1(\omega, T)}{\tilde{V}_2(\omega, T)} - 1\right) \cdot \frac{r_2}{r_1} \cdot \frac{1}{\omega^2 \varepsilon_0 \mu_0 \mu^* \cdot h \cdot d}\right] \quad (8)$$

As explained herein below, the electrical conductivity $\sigma(T)$ of the examined liquid may be determined in various ways. In some embodiments of the present invention the conductivity $\sigma(T)$ of the examined liquid is determined using equation (8). This approach is more suitable for liquids for which the value of the dielectric losses component $\in''(\omega,T)$ is relatively low (i.e., relative to the component $$\frac{\sigma(T)}{\varepsilon_0 \omega}),$$

or has a peak, at relatively high frequencies, such that the peak can be distinguished from the slope of the slope of the conductivity component. In such cases the measurements should be performed using extremely low frequency $\omega = \omega_s$ at which the inequality $$\varepsilon''(\omega_s, T) \ll \frac{\sigma(T)}{\varepsilon_0 \omega_s}$$

is satisfied, and the dielectric losses term $\in''(\omega_s,T)$ can be neglected. Then the conductivity $\sigma(T)$ of the examined liquid can be calculated as follows:

$$\sigma(T) \cong -2\varepsilon_0 \omega_S \text{Im}\left[\left(\frac{W_2}{W_1} \cdot \frac{\tilde{V}_1(\omega, T)}{\tilde{V}_2(\omega, T)} - 1\right) \cdot \frac{r_2}{r_1} \cdot \frac{1}{\omega^2 \varepsilon_0 \mu_0 \mu^* \cdot h \cdot d}\right] \quad (9)$$

If, however, the dielectric losses component $\in''(\omega,T)$ is relatively high, or has a peak, at relatively low frequencies, the electric conductivity may be determined using a differential and/or curve fitting approach, as will be now explained hereinbelow.

According to some possible embodiments of the present invention a differential measurement method is employed, wherein measurements are performed at two sufficiently close frequencies $\omega_1$ and $\omega_2$ at which the condition $\in''(\omega_1,T) \approx \in''(\omega_2,T)$ is satisfied. In this case the conductivity $\sigma(T)$ can be presented as follows:

$$\sigma(T) \cong -2\varepsilon_0 \frac{\omega_1 \omega_2}{\omega_2 - \omega_1} [\Phi(\omega_1, T) - \Phi(\omega_2, T)], \text{ where} \quad (10)$$

$$\Phi(\omega, T) = -\text{Im}\left[\left(\frac{W_2}{W_1} \cdot \frac{\tilde{V}_1(\omega, T)}{\tilde{V}_2(\omega, T)} - 1\right) \cdot \frac{r_2}{r_1} \cdot \frac{1}{\omega^2 \varepsilon_0 \mu_0 \mu^* \cdot h \cdot d}\right] \quad (11)$$

In the case of multi-frequency measurements (i.e., if more than two frequencies are used in the measurements) a fitting procedure can be applied. The function $f(\omega)=\in"(\omega,T)+A/\omega$ with the appropriate model for the dielectric losses component $\in"(\omega,T)$ can be fitted to experimental function of frequency in the right part of equation (8). Then, conductivity is presented by means of a fitting parameter A as follows:

$$\sigma(T) = A \cdot \varepsilon_0 \quad (12)$$

If two or more frequencies are used for determining the electrical conductivity of the examined material (i.e., employing the above described differential and/or curve fitting approaches), then these frequencies may be chosen within the low frequency range according to known properties of the examined material.

In a possible embodiment the primary core (50) and coil (49) of the low frequency sensor may be located inside a pipe in which the examined liquid flows, and its secondary core (51) and coil (52) inside the primary coil and core arrangement and concentric to the primary core. The sensitivity can be further increased by adding additional coils in the measurement zone to form a plurality of primary/secondary low frequency sensing units therein. Such configuration of plurality of primary/secondary low frequency sensing units may be used to concurrently measure several electric current (or voltage) signals induced within the examined liquid 23, for example, to cover a certain band of frequencies. In such possible embodiments, employing a plurality of inductively coupled primary and secondary coils in the sensing device, the design of the sensing device may be modified to prevent/minimize interferences to the electric/electromagnetic fields induced by adjacent pairs of coils, and thereby enable to concurrently measure a plurality electric signals being responsive to a respective plurality of concurrently induced electric/electromagnetic fields. For example, and without being limiting, the distance between each pair of primary and secondary coils within the cavity of the sensing device may be adjusted to substantially reduce possible influence on the induced fields, or alternatively, each pair of primary and secondary coils may be located separately in a dedicated and electrically isolated chamber formed inside the cavity of the sensing device. In this way, measured data corresponding to a certain band of frequencies may be quickly acquired and then used in the control unit to determine electrical conductivity over the selected spectrum of frequencies.

It is, however, noted that such spectral analysis may be similarly carried out utilizing a single low frequency electrical current (or voltage) sensing unit 7a by applying over the primary coil 13a a series of electric AC signals of different frequencies covering a selected band of frequencies, and serially measuring and processing the corresponding electric signals induced within the examined liquid.

In some applications, such spectral analysis of the electrical conductivity of the examined liquid 23 is utilized to determine the at least one physical property or chemical condition with improved accuracy and reliability.

Figure 2F:
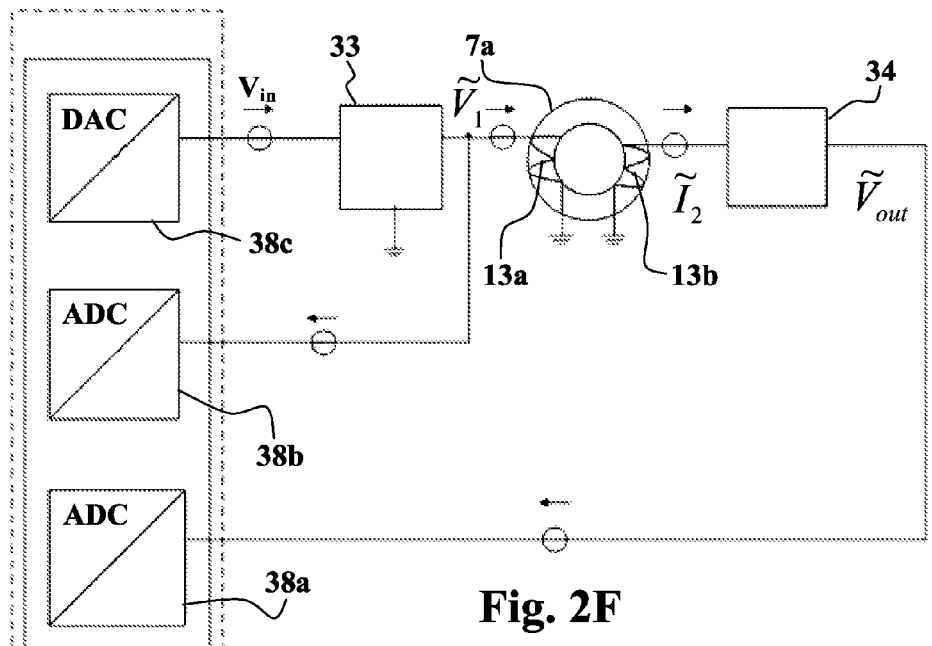

FIG. 2F schematically illustrates possible circuitry usable for applying low frequency electrical signals to primary coil 13a of sensing unit 7a and measuring the electric current induced in the secondary coil 13b. In this example a signal processing unit 38 (e.g., a DAQ 6110 card of National Instruments or other suitable instrument) is employed together with a personal computer 39 to apply electric AC signals $\tilde{V}_1$ by means of signal generator circuitry 33, and measure the responsive induced electric current $\tilde{I}_2$ by means of signal receiver circuitry 34. Signal processing unit 38 may include a digital to analog converter (DAC) 38c used to provide an input voltage signal $V_{in}$ to signal generator circuitry 33, a first analog to digital converter 38b used to acquire samples of the electric AC signals $\tilde{V}_1$ produced by signal generator circuitry 33 and applied over primary coil 13a, and a second analog to digital converter 38a used to acquire samples of the electric AC voltage $\tilde{V}_{out}$ measured over the secondary coil 13b by signal receiver 34.

Figure 2G:
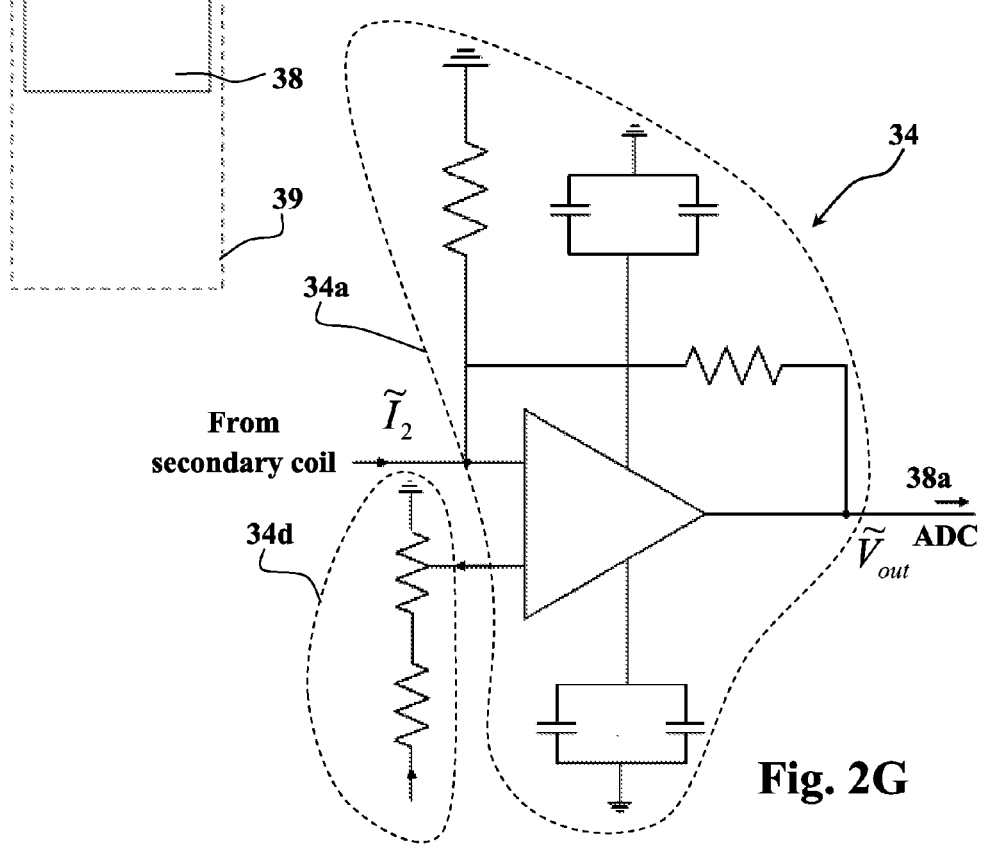

Possible implementation of signal receiver circuitry 34 is shown in FIG. 2G. In this example the induced AC current $\tilde{I}_2$ is amplified by amplifier circuitry 34a (e.g., using non-inverting operational amplifier) having a calibrating circuitry 34d.

Figure 2H:
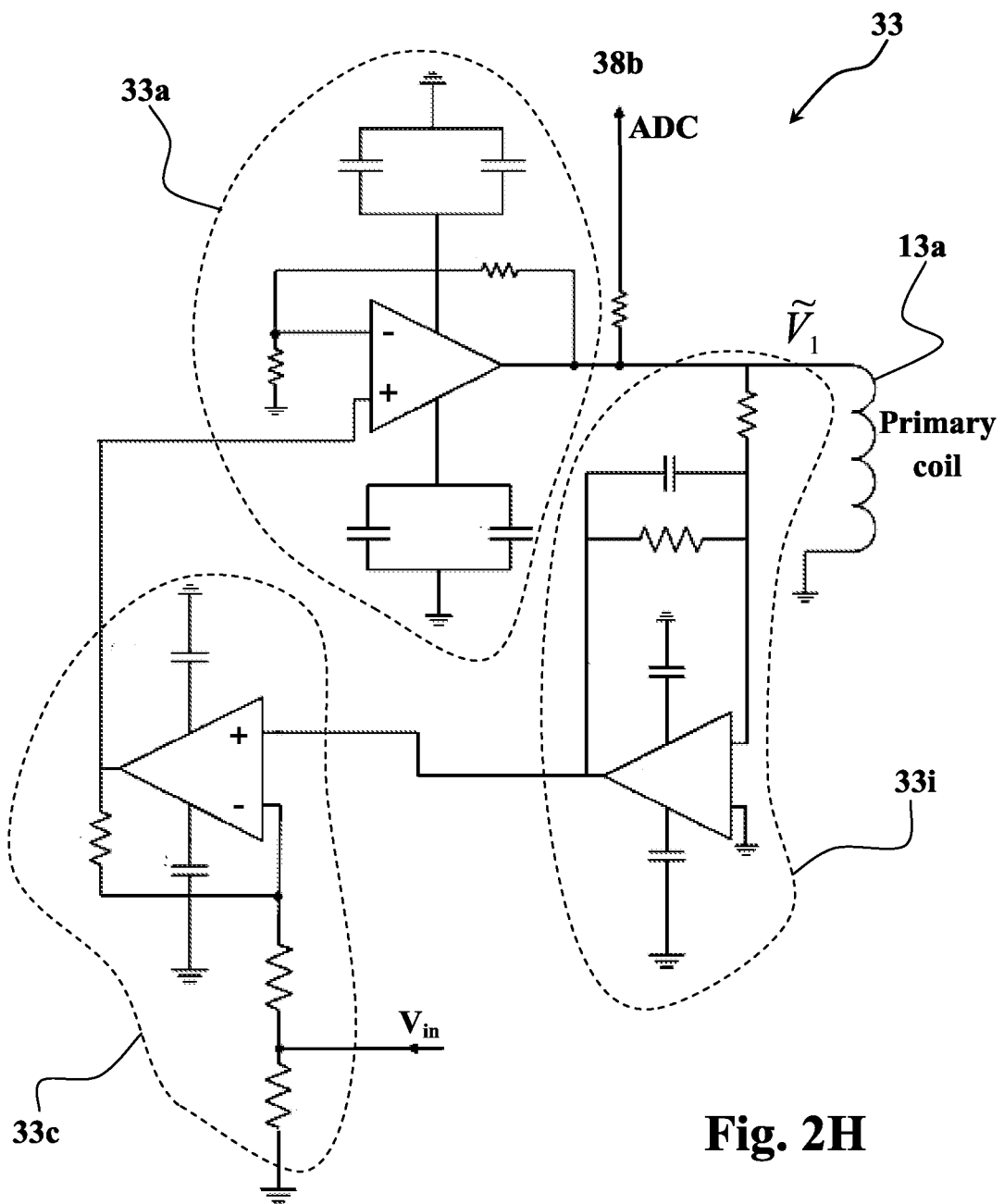

Possible implementation of signal generator circuitry 33 is shown in FIG. 2H. In this example an oscillating signal is generated utilizing integrator circuitry 33i which receives the electric signal $\tilde{V}_1$ supplied to coil 13a as its input, a differential circuit 33c (e.g., differential amplifier) receiving the input voltage signal $V_{in}$ produced by DAC 38c (see FIG. 2F) and the signal outputted from integrator 33i as its inputs, and an amplifying circuitry 33a which receives the output signal of differential circuitry 33c as its input and generates the electric signal $\tilde{V}_1$ supplied to coil 13a. In this way a feedback loop is obtained using the circuitries 33i, 33c and 33a, configured to apply a predefined voltage $\tilde{V}_1$ over the primary coil 13a according to the input voltage signal $V_{in}$ from the DAC 38c. Of course other configurations and circuitry designs may be utilized to implement signal generator circuitry 33.

The inductive sensor configuration exemplified in FIGS. 2A-E overcomes problems associated with regular contact electrodes when used in complex liquids (e.g., milk). For example, contact electrodes can become clogged with fatty deposits, degrading the level of the signal and requiring frequent cleaning, usually using aggressive materials. Another problem associated with contact electrodes typically occur when the level of salt is significant in the liquid flow, which may cause ions accumulation along the electrode interface such that the electric field between the electrodes falls mainly on the thin layer close to the electrodes where the ions have accumulated. This leads to a phenomena called Electrode Polarization wherein the sensor actually measures the capacitance of this narrow layer, rather than the bulk sample.

Figure 3:
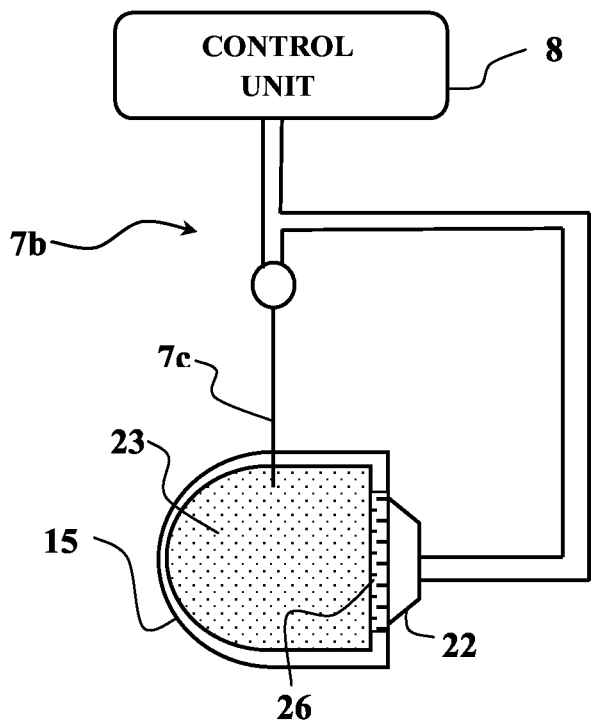
FIG. 3 is a schematic illustration of a sensing unit configured for measuring reflection (or absorbance) of high frequency electromagnetic radiation according to a possible embodiment of the present invention.

Reference is now made to FIG. 3 exemplifying a second sensor unit 7b configured as a microwave sensor, i.e., high frequency electromagnetic reflectivity sensing unit. In this example the sensing unit 7b is configured for measuring reflectivity (e.g., scattered parameter $S_{11}$) of the examined liquid 23 being indicative of the quantity of bulk water in the examined liquid (e.g., milk). This measurement is carried out by determining the phase shift and ratio of magnitudes between a transmitted and reflected electromagnetic radiation signals at a frequency in the range of 2 to 70 GHz. For example and without being limiting, by measuring the reflection coefficient, $S_{11}$, at a frequency of approximately 35 GHz, a related dielectric permittivity can be determined according to the following equation:

$$\sqrt{\varepsilon} = \frac{1-S_{11}}{1+S_{11}}, \quad (12)$$

The humidity level (i.e., water content) in the examined liquid may be estimated by comparing the value of the dielectric permittivity $\in$ computed based on the reflectivity measurement to the dielectric permittivity of water (~80*$\in_0$) e.g., using appropriate calibration/reference data.

In the example illustrated in FIG. 3 the sensing unit 7b is attached to a pipe 15 containing a liquid sample 23 (e.g., through which the sample flows). The pipe 15 is made of a suitable material, or has a region thereof at a location where the sensor 7b is placed made of said material (e.g., made of Teflon or quartz), to form a window 26 for the radiation access to and from the sample inside the pipe 15. The sensing unit 7b includes an antenna circuit (transmitter/receiver) 22 for transmitting radiation into the sample 23 and receiving reflected radiation, and generating data indicative of the received radiation. The antenna circuit 22 may be configured for generation of probing signals, and for receiving and processing responsive reflected signals, and may include inter alia signal amplifier, filter, etc. An external, or internal, signal source (not shown) may be used for supplying high frequency (e.g., in the 2 to 70 GHz range) electrical signals to antenna circuit 22 for generation of the probing signals.

The received reflected signal is processed (either in the external control unit 8 to which the sensor 7b is connected or by an in inside chip (processor) within the sensor unit, as the case may be), to determine the reflection coefficient of the examined liquid. At frequencies of about 2 GHz the dielectric permittivity is dominated by the presence of water. For example, if the pipe 15 is filled only with water, then the calculated permittivity would be ~80 (depending on the temperature condition).

The dielectric permittivity is a function of temperature. Accordingly, a temperature sensing unit 7c is preferably provided to enable more precise measurements of the desired parameters.

It is, however, noted that the permittivity of the examined liquid may be determined by measuring absorbance (e.g., scattered parameter $S_{12}$) of the transmitted electromagnetic radiation on the examined liquid 23. In this case, an additional antenna (not shown) placed on the other side of the pipe 15, opposite to antenna 22, may be used for measuring the phase shift and magnitude of electromagnetic radiation passed through the examined liquid 23 responsive to electromagnetic radiation signal transmitted from the antenna 22.

By way of example, considering that the examined liquid 23 is milk, then there are other ingredients in the sample such as fat, that reduce the water content in the examined liquid, and the measured permittivity therefore will be less than the permittivity of pure water. The ratio of measured permittivity to water permittivity is directly proportional to the water content in the examined liquid. To this end, the temperature measurement is used for accurately selecting the value of water permittivity to be used as a reference for estimating the humidity level of the examined liquid.

Figure 4:
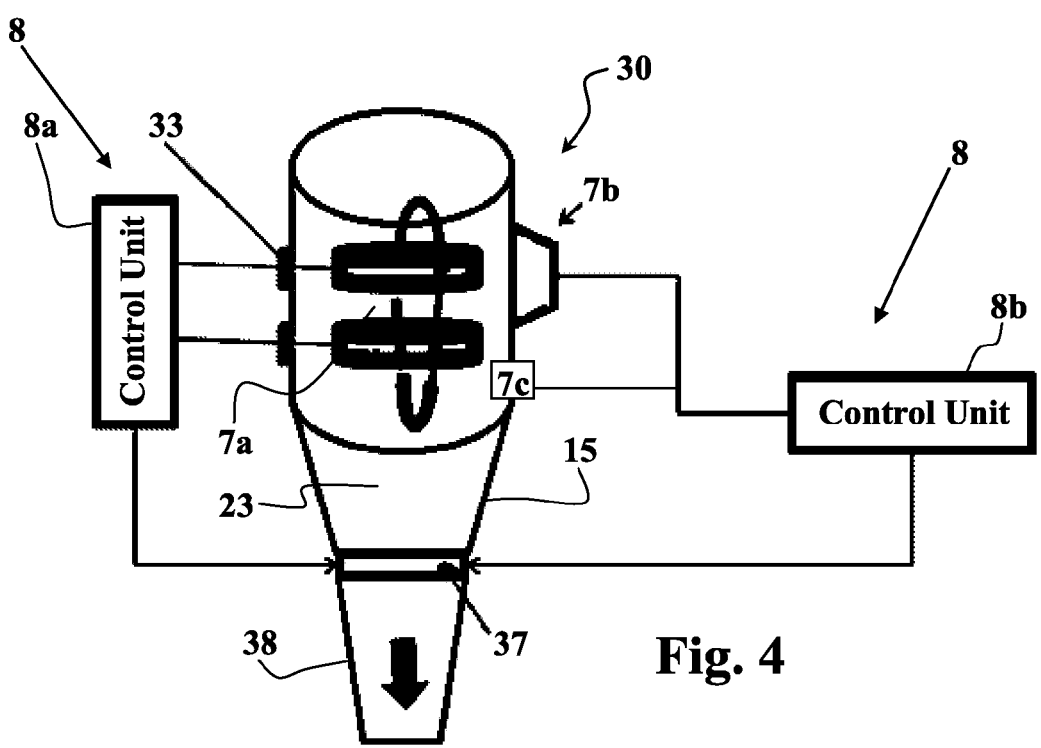
FIG. 4 is a schematic illustration of a real-time onsite measurement system for determining properties of a streamed complex liquid according to some possible embodiments of the present invention.

As indicated above, the present invention may be implemented as an online onsite measurement system for measuring in real-time chemical conditions, physical properties, and/or determine quality of a complex liquids during their flow on a production line. A specific but not limiting example of the implementation of such a system 30 is schematically illustrated in FIG. 4. System 30 includes a sensing device including multiple sensor units which include the low frequency sensing unit 7a (e.g., using any one of the sensor configurations illustrated in FIGS. 2A-2F), high frequency sensing unit 7b (e.g., microwave sensor, as illustrated in FIG. 3), and temperature sensor 7c (e.g., installed inside the pipe in direct contact with the examined liquid 23, or over an external wall region of the pipe). System 30 may be installed in a bypass pipe, and may be linked to a control unit 8, such as, but not limited to, a PC (personal computer) and/or a PLC (programmable logic controller), or any other suitable controller or control logic.

In this example, the examined liquid is passed through the pipe 15 which has an appropriate window for radiation transmission. The low frequency sensor unit 7a is placed inside the pipe (e.g., attached to an inner surface of the pipe) while the high frequency sensor 7b is mounted on the outer surface of the pipe and communicates with the inside thereof via the window. Based on measurements obtained from the low frequency sensor 7a and high frequency sensor 7b, various physical properties and chemical conditions of the examined liquid 23 can be calculated/determined by control unit 8. In the present non-limiting example, the control unit 8 is shown as including two separate controllers/processors 8a and 8b associated with the two sensor units respectively.

For example and without being limiting, the control unit 8 may determine whether the liquid streamed through pipe 15 is tainted with bacterial infection and estimate the fat content. Measured data obtained using the high frequency sensor 7b may be used to estimate the water content in the examined liquid. The control unit 8 includes a processor (not shown) receiving measured/processed data from controllers 8a and 8b and operates to determine and possibly also display data indicative of the quality of the examined liquid. Based on the measured data, and the determined physical parameters and/or chemical conditions of the examined liquid, the control unit 8 may produce control signals for adjusting the state of a valve 37 installed in pipe 15 in order to regulate, or halt, the passage of the liquid through an outlet 38 thereof.

It should be understood that although FIG. 4 illustrates two separate controllers/processors, a single processor can be used for receiving measured data pieces from different sensors. The control unit 8 may be incorporated in or configured as any suitable controller, MCU, PC, control logic, configured to implement the various units and sub-units, or by any suitable control unit having processing means (e.g., CPU) and memory means (e.g., RAM, ROM, FLASH, and suchlike) storing one or more programs and data used for implementing the various units and subunits.

Figure 5:
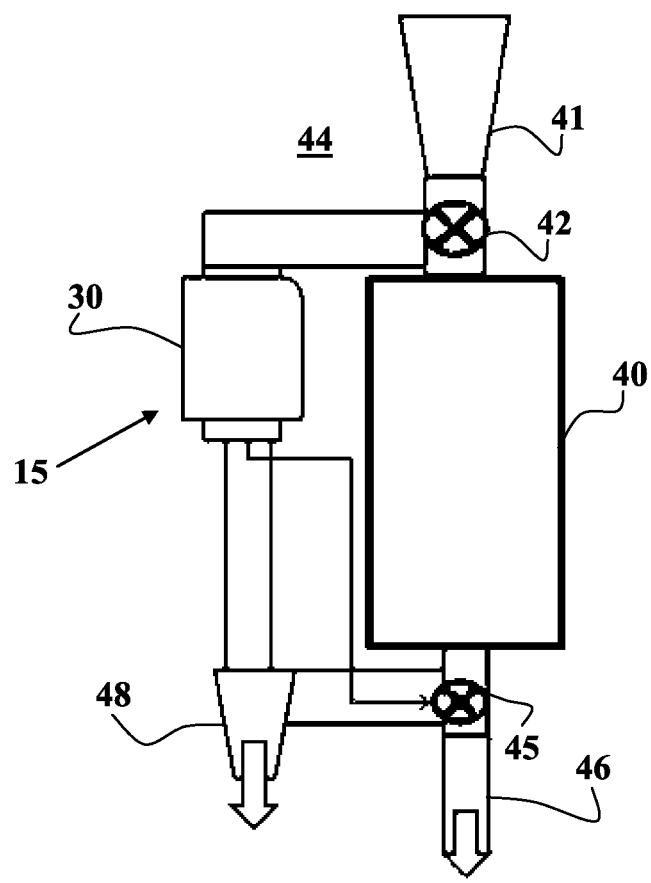
FIG. 5 is a schematic illustration of a liquid quality measurement and stream directing system according to another possible embodiment of the present invention.

FIG. 5 schematically illustrates an example of a liquid flow arrangement 44 having a main pipe or tank 40 and a bypass pipe 15 into which a liquid flow is selectively directed via a valve 42. The main and bypass pipes 40 and 15 have outlets 46 and 48 respectively, and the output of the bypass pipe 15 can be selectively connected to and disconnected from the main pipe via a valve 45. A monitoring system 30 of the present invention is associated with the bypass pipe 15 similar to the example of FIG. 4 and operates to take measurements of a liquid streamed through bypass pipe 15 into the main pipe or tank 40. In this example the control valve 42 is used in inlet pipe 41 for directing a liquid sample to the multi sensor monitoring system 30 mounted on the bypass pipe 15.

The multi sensor monitoring system 30 may comprise any combination of the sensors arrangements described hereinabove and hereinbelow (e.g., as exemplified in FIGS. 1A-B and 2A-H) and a controller for processing the measurement data generated by the sensors, determining one or more properties of the examined liquid based thereon, and generating control signals responsively e.g., to set the states of the valves 42 and/or 45.

Depending on the determined physical properties and/or chemical conditions of the examined liquid, the liquid is allowed to proceed to an appropriate container (not shown) or is discarded, via the operation (controllable) of the valve 45.

Figure 6:
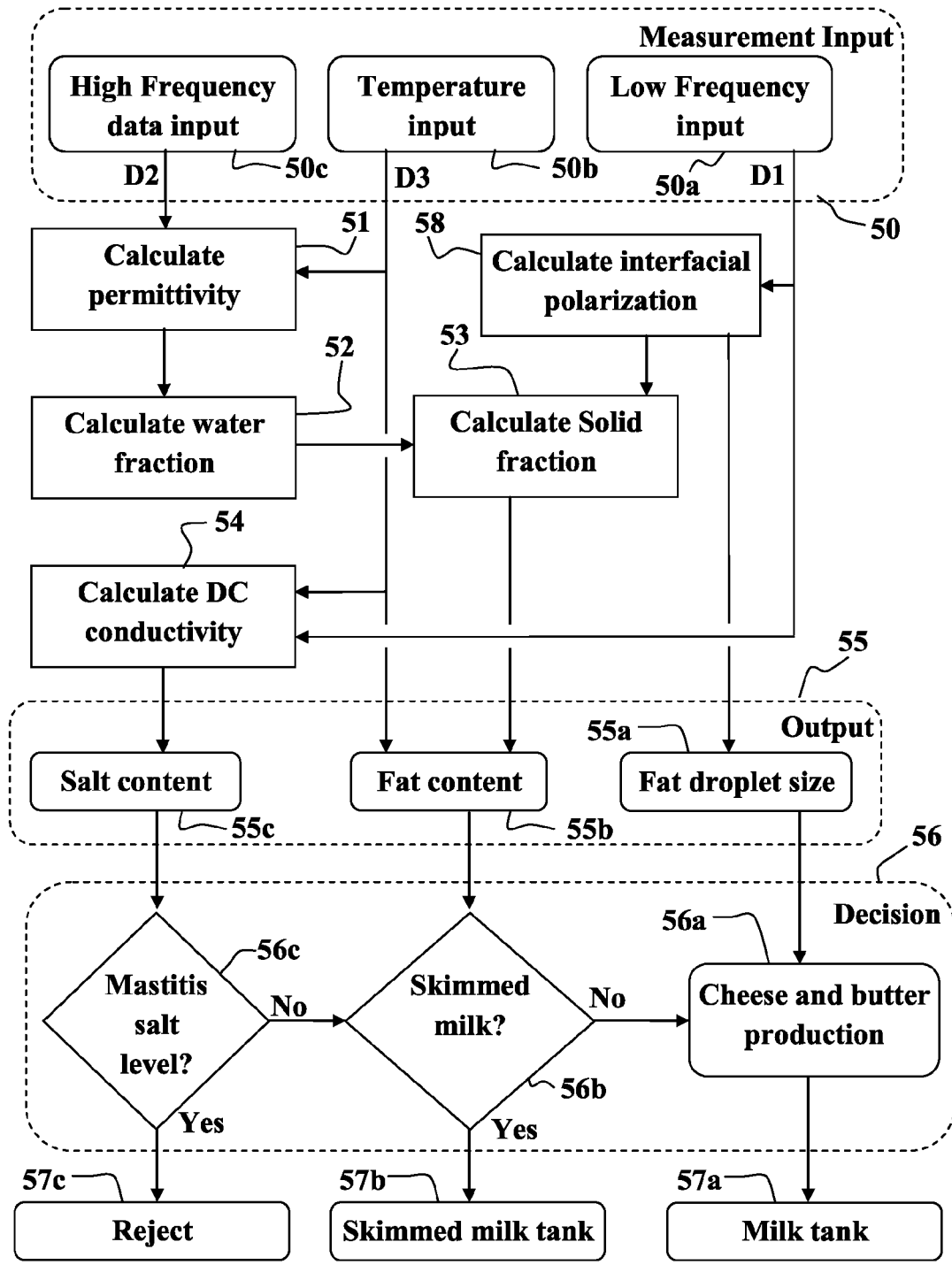
FIG. 6 is a flowchart exemplifying a process according to some possible embodiments of the present invention for measuring and calculating various properties of the examined liquid, and based thereupon, determining further processing steps.

FIG. 6 is a flowchart schematically illustrating a possible process of operation of the monitoring system of the invention for determining at least one physical property or chemical condition of a complex liquid and deciding about further processing of the examined liquid (e.g., directing it to a suitable container) accordingly. Measured data is provided (step 50) from the sensing device including measured data D1 indicative of the induced low frequency electric/electromagnetic signal, measured data D2 indicative of a high frequency electromagnetic reflectivity measurement, and measured data D3 indicative of a temperature measurement. It is noted that other, or additional, parameters may be measured, other than those illustrated in FIG. 6.

The measured data is processed, and output data is generated (step 55) indicative of various physical properties and/or chemical conditions of the examined liquid, including for example, fat droplet size 55a; fat content 55b; and salt content 55c.

In this non-limiting example, the processing of the input measured data is carried out as follows. The low frequency measurement data D1 and the temperature measurement data D3 are used (step 54) for calculating electrical conductivity of the examined liquid, from which salt content 55c is determined (e.g., as described in "*Electrical conductances of aqueous sodium chloride solutions from 0 to 800.degree. and at pressures to 4000 bars*" J. Phys. Chem., 1968, 72 (2), pp 684-703, and in "*Computation of Electrical Conductivity of Multicomponent Aqueous Systems in Wide Concentration and Temperature Ranges*", Ind. Eng. Chem. Res., 1997, 36 (5), pp 1932-1943). The high frequency reflectivity measurement data D2 (e.g., reflection coefficient $S_{11}$) and temperature measurement data D3 are used (step 51) for calculating dielectric permittivity of the examined liquid (e.g., using equation (12) above), which may be used to estimate water fraction/content in the examined liquid (step 52), for example, by comparing the value of the calculated dielectric permittivity to that expected for water. For example and without being limiting, in some embodiments the temperature of the examined liquid 23 and its dielectric permittivity (e.g., determined using the high frequencies electromagnetic radiation measurements) are combined to determine the water content.

Based on the calculated water fraction (step 52) and interfacial polarization (step 58), solid fraction of the examined liquid may be determined (step 53), which may be used to determined the fat content 55b, optionally using the measured temperature measured data D3. Also, interfacial polarization may be determined (step 58) based on the measurements indicative of the induced low frequency electric field measurement data D1 and an appropriate mixture formula (see, e.g., T. Hanai, "*Theory of the dielectric dispersion due to the interfacial polarization and its application to emulsions*" by Kolloid-Zeitschrift, 1960, Band 171, Heft 1, 23-31, and T. Hanai and K. Sekine "*Theory of dielectric relaxation due to the interfacial polarization for two-component suspensions of spheres*" Colloids & Polymer Science 1986, 24, 888-895). The interfacial polarization 58 can be used to determine the fat droplet size (step 55a), using the same mixture formulas as stated previously.

The determined fat droplet size (step 55a), fat content (step 55b) and salt content (step 55c) may be then used for decision making (step 56) concerning further processing of the examined liquid, if so needed. For example, if the examined liquid is milk, salt content 55c may be used for checking whether the salt level in the batch of extracted milk is higher than acceptable (step 56c e.g., Mastitis salt level defined by a conductivity level of more than 6.5 mS/cm, M. Janzekovic et. al., JAMME 34 (2009), 39-46), and if so, to reject the milk batch obtained from the milked cow (step 57c), e.g., direct it to a disposal pipe or container. Otherwise, if it is determined that the salt level is acceptable, the system then operates to check based on fat content 55b, whether the fat content is low (e.g., less than 2% by volume) or high (e.g., higher than 10%), as exemplified in step 56b. If a low fat content is identified, then the milk batch from the milked cow is directed to a skimmed milk container (step 57b). Otherwise, if a high fat content is determined, the milk batch extracted from the milked cow is directed to a suitable milk container 57a for further processing (e.g., in cheese or butter production lines).

It is noted that in settings currently used in automated milking applications it is custom to extract a sample obtained from a tank containing milk extracted from a number of concurrently milked cows (e.g., four cows), and send the same to a laboratory test to determine the quality of the extracted milk. It is obvious that such quality tests are time consuming and may result in the disposal of substantial amounts of milk e.g., more than 40 liters of milk assuming three milking sessions per day for an average milking cow, if bad milk qualities are determined. On the other hand, the present invention allows to quickly determined the quality of milk extracted from each individual cow (also referred to herein as a batch of milk) and decide accordingly if the quality of the milk extracted from a specific cow is acceptable, and if so, decide on further processing of the extracted milk. In this way, if it is determined that the quality of the extracted batch of milk is not acceptable, a relatively small amount of extracted milked needs to be disposed (e.g., about 10 liters).

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A system for determining at least one property of a complex liquid, the system comprising:
   a sensing device comprising
      a first sensing unit comprising at least one pair of induction coils configured and operable for inductively inducing an electric field inside said liquid, measuring an electrical response of said liquid to the inductively induced electric field, and generating first measured data indicative thereof, and
      a second sensing unit comprising at least one electromagnetic transceiver arrangement configured and operable for applying an electromagnetic field to said complex liquid, measuring at least one of electromagnetic absorbance and reflectivity of the liquid responsive to the applied electromagnetic field, and generating second measured data indicative thereof; and a control unit configured and operable for receiving and analyzing said first and second measured data from the sensing device and determining at least a solid fraction of said complex liquid.

2. The system of claim 1, wherein the control unit is configured and operable to determine either electrical impedance or conductivity using the first measured data indicative of the inductively induced electric field.

3. The system of claim 1, wherein the control unit is configured and operable to determine the salt content based on the first measured data indicative of the inductively induced electric field.

4. The system of claim 1, wherein the control unit is configured and operable to determine dielectric permittivity of the liquid based on the second measured data indicative of the applied electromagnetic field.

5. The system of claim 4 wherein the control unit is configured and operable to select a frequency range of the inductively induced electric field to minimize dielectric losses of a complex dielectric permittivity component $\sigma(T)/\in_0 \omega$ of the dielectric permittivity, where $\sigma(T)$ designates conductivity, $\in_0$ designates dielectric permittivity of free space, and $\omega$ designates the frequency.

6. The system of claim 1 wherein the first sensing unit comprises a plurality of the inductively coupled coils configured and operable to concurrently induce a plurality of electric fields each at a different frequency to thereby cover a predefined range of frequencies associated with the electric fields and measure a respective plurality of electrical responses to the inductively induced electric fields, and wherein the control unit is configured and operable to determine the at least one property of the liquid based on said plurality of electrical responses.

7. The system of claim 1 wherein a frequency range of the electromagnetic field is selected for determining at least one of S11 and S21 parameters by detection of phase shifts and magnitudes of microwave signals transmitted through the liquid.

8. The system of claim 7 wherein the frequency range is about 2 to 70 GHz.

9. The system of claim 1, wherein the sensing device is configured and operable for measuring temperature of the liquid and generating data indicative thereof.

10. The system of claim 9 wherein the control unit is configured and operable to determine the permittivity of the liquid based on the second measured data indicative of the applied electromagnetic field and the data indicative of the measured temperature.

11. The system of claim 1 wherein the control unit is configured and operable to determine fat droplet size and interfacial polarization of the liquid based on the first measured data indicative of the inductively induced electric field.

12. The system of claim 4 wherein the control unit is configured and operable to determine at least one of water and fat content of the liquid based on the determined permittivity.

13. The system of claim 1 wherein the control unit is configured and operable to determine electrical conductivity of the liquid using either differential computation or curve fitting methods based on two or more measurements of electrical voltages inductively induced through the examined liquid responsive to respective two or more inductively induced electric fields of different frequencies.

14. The system of claim 1 wherein the control unit is configured and operable to determine whether to transfer the liquid for further processing based on the determined at least one property of the liquid, and generate control signals for processing the liquid by the system accordingly.

15. A method for determining at least one property of a complex liquid, the method comprising:
    inductively inducing an electric field inside said liquid by at least one pair of induction coils;
    measuring, using the at least one pair of induction coils, a response of said liquid to the electric field inductively induced in said liquid to generate first measured data indicative thereof;
    applying an electromagnetic field to said complex liquid by an electromagnetic transceiver arrangement;
    measuring, using the electromagnetic transceiver arrangement, a response of said liquid to the applied electromagnetic field to generate second measured data indicative thereof; and
    processing said first and second measured data by a control unit to determine said at least one property, where said at least one property comprises a solid fraction of the liquid.

16. The method of claim 15 comprising determining whether to transfer the liquid for further processing based on said at least one property.

17. The method of claim 15 further comprising measuring temperature of the liquid to determine the at least one property of the liquid.

18. The method of claim 15 wherein the at least one property further comprises at least one of the following: electric impedance, electrical conductivity, electrical admittance, permittivity, interfacial polarization, fat droplet size, salt content, water content and fat content.

19. The method of claim 18, further comprising:
    measuring temperature of the liquid; and
    determining the permittivity of the liquid based on the response to the electromagnetic field and the measured temperature of the liquid.

20. The method of claim 18 further comprising determining at least one of the fat droplet size and the interfacial polarization of the liquid based on the response to the inductively induced electric field.

21. The method of claim 18 further comprising determining at least one of the water and fat content of the liquid based on the determined permittivity.

22. The method of claim 18 further comprising measuring temperature of the liquid and determining at least one of the electrical conductivity and the salt content of the liquid based on the response to the inductively induced electric field and the measured temperature of the liquid.

23. A piping system defining a main path for streaming a complex liquid therethrough, the piping system comprising:
    a sensing device comprising a first sensing unit configured for locating inside the main path and a second sensing unit configured to be accommodated in the vicinity of said main path and outside thereof, the first sensing unit comprises at least one pair of induction coils configured and operable for inducing an electric field inside said liquid, measuring electrical response of said liquid to the inductively induced electric field and generating first measured data indicative thereof, and the second sensing unit comprising at least one electromagnetic transceiver arrangement configured and operable for applying an electromagnetic field to said liquid flowing through the main path and measuring either electromagnetic absorbance or reflectivity responsive to the applied electromagnetic field and generating second measured data indicative thereof; and a control unit connectable to said sensing device for receiving and analyzing said first and second measured data, determining at least a solid fraction of said complex liquid, and generating data indicative of quality of the liquid being streamed through said main path, thereby enabling generation of sorting data of the liquid while being streamed through the main path of said piping system.

* * * * *